(12) United States Patent
He et al.

(10) Patent No.: US 8,217,183 B2
(45) Date of Patent: Jul. 10, 2012

(54) METHODS OF MAKING FUSED THIOPHENES

(75) Inventors: Mingqian He, Horseheads, NY (US); Jieyu Hu, Painted Post, NY (US); James R. Matthews, Painted Post, NY (US); Weijun Niu, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 263 days.

(21) Appl. No.: 12/782,055

(22) Filed: May 18, 2010

(65) Prior Publication Data
US 2011/0288306 A1    Nov. 24, 2011

(51) Int. Cl.
*C07D 409/14* (2006.01)
(52) U.S. Cl. .......................................... 549/42
(58) Field of Classification Search ............... 549/42
See application file for complete search history.

(56) References Cited

U.S. PATENT DOCUMENTS

| 7,601,279 B2 | 10/2009 | Masuda | 252/500 |
| 7,705,108 B2 | 4/2010 | He | 528/226 |

FOREIGN PATENT DOCUMENTS

| WO | 2006/031893 A2 | 3/2006 |
| WO | 2008/106019 A2 | 9/2008 |
| WO | 2008/106019 A3 | 9/2008 |
| WO | 2010/138650 A1 | 12/2010 |

OTHER PUBLICATIONS

Abarbri, et al., "Preparation of New Polyfunctional Magnesiated Heterocycles Using a Chlorine-, Bromine-, or Iodine-Magnesium Exchange", Journal of Organic Chemistry, 65, (2000), pp. 4618-4634.

Shchekotikhin, et al., "Heterocyclic Analogs of 5,12-Naphthacenequinone 6.* Synthesis of 4,11-Dimethoxy Derivatives of Anthra-[2,3-*b*]Thiophene-5,10-Dione and Anthra[2,3-*d*]Isothiazole-5,10-Dione", Chemistry of Heterocyclic Compounds, vol. 43, No. 4, 2007, pp. 439-444.

He, Mingqian, et al., Synthesis and Structure of Alkyl-Substituted Fused Thiophenes Containing Up to Seven Rings, J. Org. Chem., 72, 2007, pp. 442-451.

He, Mingqian, et al., "Alkylsubstituted Thenothiophene Semiconducting Materials: StructureProperty Relationships," Journal of the American Chemical Society, 131, pp. 11930-11938, 2006.

Fong, et al., Tetrathienoacene Copolymers As High Mobility, Soluble Organic Semiconductors, Journal of the American Chemical Society, 2008, 130 (40), pp. 13202-13203.

Harding, et al., Selective Oxidation of Allylic Alcohols With Chromic Acid, Journal of Organic Chemistry, vol. 40, No. 11, 1975, pp. 1664-1665.

Frey, et al., Synthesis of Dithieno[3,2-*b*:2'3'-*d*]Thiophene, Organic Syntheses, vol. 83, 2006, p. 209.

Frey, et al., Improved Synthesis of Dithieno[3,2-*b*:2'3'-*d*]Thiophene (DTT) and Derivatives for Cross Coupling, Chemical Communications, 2002, p. 2424.

*Primary Examiner* — Taofiq A Solola
(74) *Attorney, Agent, or Firm* — John L. Haack

(57) ABSTRACT

β"-di-R-substituted fused thiophene (DCXFT4) compounds, and a method for making a compound of the formula (V):

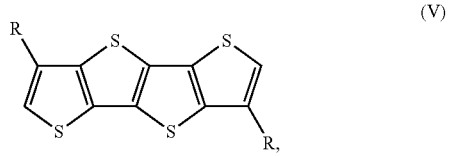

(V)

where each R is a $C_4$ to $C_{25}$ hydrocarbylene, the method including di-acylating tetra-bromo dithiophene (I); contacting the bromo-dithiophene compound (II) with a 2-mercaptoacetate to form cyclized fused thiophene (III); converting fused thiophene (III) to the corresponding diacid (IV); and decarboxylating the diacid (IV) to the fused thiophene (V), of the formulas as defined herein.

12 Claims, No Drawings

METHODS OF MAKING FUSED THIOPHENES

The entire disclosure of any publication, patent, or patent document mentioned herein is incorporated by reference.

BACKGROUND

The disclosure generally relates to methods of making fused thiophene compounds. For additional background see commonly owned and assigned, U.S. Pat. No. 7,705,108, to He, M., et al., entitled "FUSED THIOPHENES, METHODS FOR MAKING FUSED THIOPHENES, AND USES THEREOF."

SUMMARY

The disclosure provides improved methods of making fused thiophene (FT) compounds, and polymers thereof.

DETAILED DESCRIPTION

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments of the claimed invention.

Definitions

"FTx" or like abbreviations can refer to a fused thiophene compound, polymerizable monomers thereof, and polymers thereof, where x is an integer indicating the number of fused thiophene ring or cycle units fused into a single core unit, for example, an FT2 has two fused rings in the core unit, an FT3 has three fused rings in the core unit, an FT4 has four fused rings in the core unit, an FT5 has five fused rings in the core unit, and like higher designations in the core unit.

"DCXFT4" or like abbreviations represent the class of symmetrical di-beta-substituted fused thiophene compounds where X is an integer representing the di-(R) substituent, which designates the number of carbon atoms in each R substituent or group attached to the core of a 3,7,10,14-tetrathiatetracyclo[6.6.0.0$^{2,6}$.0$^{9,13}$]tetradeca-1(8),2(6),4,9(13),11-pentaene.

"DC10FT4" or like abbreviations represent the specific DCXFT4 compound: 3,7-Didecyl thieno[3,2-b]thieno[2',3':4,5]thieno[2,3-d]thiophene where the "10" represents the C$_{10}$ di-decyl substituents attached to the core (see *J. Org. Chem.*, 2007, 72, 442-451), or (IUPAC) 5,12-didecyl-3,7,10,14-tetrathiatetracyclo[6.6.0.0$^{2,6}$.0$^{9,13}$]tetradeca-1(8),2(6),4,9(13),11-pentaene.

"DC17FT4" or like abbreviations represent a specific DCXFT4 compound: 3,7-diheptadecyl thieno[3,2-b]thieno[2',3':4,5]thieno[2,3-d]thiophene, where the "17" represents each of the C$_{17}$ heptadecyl substituents attached to the core (see *J. Org. Chem.* ibid), or alternatively (following IUPAC naming conventions since FT4 compounds are not presently named), 5,12-diheptadecyl-3,7,10,14-tetrathiatetracyclo[6.6.0.0$^{2,6}$.0$^{9,13}$]tetradeca-1(8),2(6),4,9(13),11-pentaene.

"DC21FT4" or like abbreviations represent a specific DCXFT4 compound: 3,7-di-heneicosyl thieno[3,2-b]thieno[2',3':4,5]thieno[2,3-d]thiophene where the "21" represents the C$_{21}$ di-heneicosyl substituents attached to the core (see *J. Org. Chem.* ibid), or (IUPAC) 5,12-dihencosyl-3,7,10,14-tetrathiatetracyclo[6.6.0.0$^{2,6}$.0$^{9,13}$]tetradeca-1(8),2(6),4,9(13),11-pentaene.

"Hydrocarbon," "hydrocarbyl," "hydrocarbylene," "hydrocarbyloxy," and like terms generally refer to monovalent, such as —R, or divalent —R— moieties, and can include, for example, alkyl hydrocarbons, aromatic or aryl hydrocarbons, alkyl substituted aryl hydrocarbons, alkoxy substituted aryl hydrocarbons, heteroalkyl hydrocarbons, heteroaromatic or heteroaryl hydrocarbons, alkyl substituted heteroaryl hydrocarbons, alkoxy substituted heteroaryl hydrocarbons, and like hydrocarbon moieties, and as illustrated herein.

"Alkyl" includes linear alkyls, branched alkyls, and cycloalkyls. "Substituted alkyl" or "optionally substituted alkyl" refers to an alkyl substituent, which can include, for example, a linear alkyl, a branched alkyl, or a cycloalkyl, having from 1 to 4 optional substituents selected from, for example, hydroxyl (—OH), halogen, amino (—NH$_2$ or —NR$_2$), nitro (—NO$_2$), acyl (—C(=O)R), alkylsulfonyl (—S(=O)$_2$R), alkoxy (—OR), and like substituents, where R is a hydrocarbyl, aryl, Het, or like moieties, such as a monovalent alkyl or a divalent alkylene having from 1 to about 10 carbon atoms. For example, a hydroxy substituted alkyl, can be a 2-hydroxy substituted propylene of the formula —CH$_2$—CH(OH)—CH$_2$—, an alkoxy substituted alkyl, can be a 2-methoxy substituted ethyl of the formula —CH$_2$—CH$_2$—O—CH$_3$, an amino substituted alkyl, can be a 1-dialkylamino substituted ethyl of the formula —CH(NR$_2$)—CH$_3$, an oligo-(oxyalkylene), poly-(oxyalkylene), or poly-(alkylene oxide) substituted alkyl, can be, for example, of the partial formula —(R—O)$_x$—, where x can be, for example, from 1 to about 50, and from 1 to about 20, and like substituted oxyalkylene substituents, such as of the formula —(CR$^5$—CHR$^5$—O)$_x$— where R$^5$ is hydrogen or a substituted or unsubstituted (C$_{1-8}$) hydrocarbyl such as alkyl, and x is an integer of from 1 to about 50.

"Aryl" includes a mono- or divalent-phenyl radical or an ortho-fused bicyclic carbocyclic radical having about nine to twenty ring atoms in which at least one ring is aromatic. Aryl (Ar) can include substituted aryls, such as a phenyl radical having from 1 to 5 substituents, for example, alkyl, alkoxy, halo, and like substituents.

"Het" includes a four-(4), five-(5), six-(6), or seven-(7) membered saturated or unsaturated heterocyclic ring having 1, 2, 3, or 4 heteroatoms selected from the group consisting of oxy, thio, sulfinyl, sulfonyl, selenium, tellurium, and nitrogen, which ring is optionally fused to a benzene ring. Het also includes "heteroaryl," which encompasses a radical attached via a ring carbon of a monocyclic aromatic ring containing five or six ring atoms consisting of carbon and 1, 2, 3, or 4 heteroatoms each selected from the group consisting of non-peroxide oxy, thio, and N(X) wherein X is absent or is H, O, (C$_{1-4}$)alkyl, phenyl, or benzyl, and a radical of an ortho-fused bicyclic heterocycle of about eight to ten ring atoms derived therefrom, particularly a benzo-derivative or one derived by fusing a propylene, trimethylene, or tetramethylene diradical thereto.

In embodiments, halo or halide includes fluoro, chloro, bromo, or iodo. Alkyl, alkoxy, etc., include both straight and branched groups; but reference to an individual radical such as "propyl" embraces only the straight chain radical, a branched chain isomer such as "isopropyl" being specifically referred to.

The carbon atom content of various hydrocarbon-containing (i.e., hydrocarbyl) moieties can alternatively be indicated by a prefix designating a lower and upper number of carbon atoms in the moiety, i.e., the prefix C$_{i-j}$ indicates a moiety of the integer "i" to the integer "j" carbon atoms, inclusive. Thus, for example, (C$_1$-C$_8$)alkyl or C$_{1-8}$alkyl refers to an alkyl of one to eight carbon atoms, inclusive, and hydrocarbyloxy such as ($C_1$-$C_8$)alkoxy or $C_{1-8}$alkoxy refers to an alkoxy radical (—OR) having an alkyl group of one to eight carbon atoms, inclusive.

Specifically, $C_{1-8}$alkyl can be, for example, methyl, ethyl, propyl, isopropyl, butyl, iso-butyl, sec-butyl, tea-butyl, pentyl, 3-pentyl, hexyl, heptyl, or octyl; ($C_{3-12}$)cycloalkyl can be cyclopropyl, cyclobutyl, cyclopentyl, cyclohexyl, cycloheptyl, cyclooctyl, including bicyclic, tricyclic, or multi-cyclic substituents, and like substituents.

A specific "hydrocarbyl" can be, for example, ($C_{1-24}$)hydrocarbyl, including all intermediate chain lengths and values.

$C_{1-8}$alkoxy can be, for example, methoxy, ethoxy, propoxy, isopropoxy, butoxy, iso-butoxy, sec-butoxy, pentoxy, 3-pentoxy, hexyloxy, 1-methylhexyloxy, heptyloxy, octyloxy, and like substituents.

A —C(=O)($C_{3-7}$)alkyl- or —($C_{2-7}$)alkanoyl can be, for example, acetyl, propanoyl, butanoyl, pentanoyl, 4-methylpentanoyl, hexanoyl, or heptanoyl. Aryl (Ar) can be, for example, phenyl, naphthyl, anthracenyl, phenanthrenyl, fluorenyl, tetrahydronaphthyl, or indanyl. Het can be, for example, pyrrolidinyl, piperidinyl, morpholinyl, thiomorpholinyl, or heteroaryl. Heteroaryl can be, for example, furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for Het includes a five-(5), six-(6), or seven-(7) membered saturated or unsaturated ring containing 1, 2, 3, or 4 heteroatoms, for example, non-peroxide oxy, thio, sulfinyl, sulfonyl, selenium, tellurium, and nitrogen; and a radical of an ortho-fused bicyclic heterocycle of about eight to twelve ring atoms derived therefrom, particularly a benzo-derivative or one derived by fusing a propylene, trimethylene, tetramethylene, or another monocyclic Het diradical thereto.

Other conditions suitable for formation and modification of the compounds, oligomers, polymers, composites or like products of the disclosure, from a variety of starting materials or intermediates, as disclosed and illustrated herein are available. For example, see Feiser and Feiser, "Reagents for Organic Synthesis", Vol. 1, et seq., 1967; March, J. "Advanced Organic Chemistry," John Wiley & Sons, $4^{th}$ ed. 1992; House, H. O., "Modem Synthetic Reactions," $2^{nd}$ ed., W. A. Benjamin, New York, 1972; and Larock, R. C., "Comprehensive Organic Transformations," $2^{nd}$ ed., 1999, Wiley-VCH Publishers, New York. The starting materials employed in the preparative methods described herein are, for example, commercially available, have been reported in the scientific literature, or can be prepared from readily available starting materials using procedures known in the field. It may be desirable to optionally use a protecting group during all or portions of the above described or alternative preparative procedures. Such protecting groups and methods for their introduction and removal are known in the art. See Greene, T. W.; Wutz, P. G. M. "Protecting Groups In Organic Synthesis," $2^{nd}$ ed., 1991, New York, John Wiley & Sons, Inc.

"Monomer," "mer," or like terms refer to a compound that can be (or has already been) covalently combined or linked with other monomers of like or different structure to form homogenous (homopolymers) or heterogenous (e.g., copolymers, terpolymers, and like heteropolymers) chains of the target polymer. Suitable monomers as disclosed and illustrated herein can include, for example, low molecular weight polymerizable compounds, such as from about 50 to about 200 Daltons, and higher molecular weight compounds, such as from about 200 to about 10,000 Daltons, including unsaturated oligomeric or unsaturated polymeric compounds.

"Include," "includes," or like terms means encompassing but not limited to, that is, inclusive and not exclusive.

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example: through typical measuring and handling procedures used for making compounds, compositions, composites, concentrates or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture. The claims appended hereto include equivalents of these "about" quantities.

"Consisting essentially of" in embodiments refers, for example, to a compound, to a polymer or a copolymer composition derived from the monomer compound, to a method of making or using the compound, the polymer, a formulation, or a composition, and articles, devices, or any apparatus of the disclosure, and can include the components or steps listed in the claim, plus other components or steps that do not materially affect the basic and novel properties of the compositions, articles, apparatus, or methods of making and use of the disclosure, such as particular reactants, particular additives or ingredients, a particular agent, a particular surface modifier or condition, or like structure, material, or process variable selected. Items that may materially affect the basic properties of the components or steps of the disclosure or that may impart undesirable characteristics to the present disclosure include, for example, no or very low monomer solubility, extensive or protracted purification processing because of poor solubility, unnecessary exposure of the resulting polymer to excessively high temperatures, and like contrary steps.

The indefinite article "a" or "an" and its corresponding definite article "the" as used herein means at least one, or one or more, unless specified otherwise.

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, and like abbreviations).

Specific and preferred values disclosed for components, ingredients, additives, and like aspects, and ranges thereof, are for illustration only; they do not exclude other defined values or other values within defined ranges. The compositions, devices, apparatus, and methods of the disclosure can include any value or any combination of the values, specific values, more specific values, and preferred values described herein.

Highly conjugated organic materials, such as monomer or polymer compositions of the present disclosure, are being developed for use in a variety of applications, including for example field effect transistors (FETs), thin-film transistors (TFTs), organic light-emitting diodes (OLEDs), electro-optic (EO) applications, as conductive materials, as two photon mixing materials, as organic semiconductors, and as non-linear optical (NLO) materials. Highly conjugated organic materials can be used, for example, in devices such as RFID tags, an electroluminescent device, such as used in a flat panel display, a photovoltaic, a sensor, and like devices, or a combination thereof.

In embodiments, the disclosure provides a method for making a β"-di-R-substituted fused thiophene compound.

In embodiments, one exemplary process is illustrated in Scheme 2 below.

In embodiments, the disclosure provides a method for making a symmetrical or unsymmetrical di-β"-R-substituted fused thiophene compound, including, for example:

di-acylating the tetra-bromo dithiophene of the formula (I) (an FT2 compound):

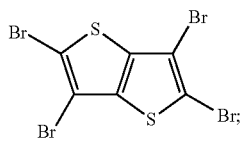
(I)

contacting the resulting α-di-acyl-β-di-bromo-dithiophene compound of the formula (II):

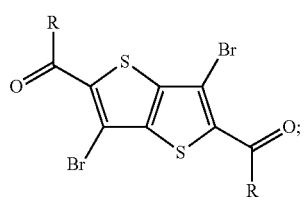
(II)

with, for example, a 2-mercaptoacetate, or like synthon, to form the cyclized α"-carboxy-β"-R-substituted fused thiophene of the formula (III) (an FT4 compound):

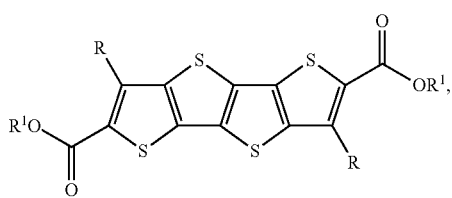
(III)

where $R^1$ is independently a substituted or unsubstituted, branched or unbranched, $C_1$ to $C_6$ hydrocarbylene, a specific example of the α"-carboxy-β"-R-substituted fused thiophene of the formula (III) is the dicarboethoxy compounds where each $R^1$ is ethoxy or like protecting groups, such as -Me, -propyl, -Bu, i-Bu, -t-Bu, and like groups;

converting the α"-carboxy-β"-R-substituted fused thiophene (III) to the corresponding diacid of the formula (IV), by for example hydrolysis or like deprotection methods:

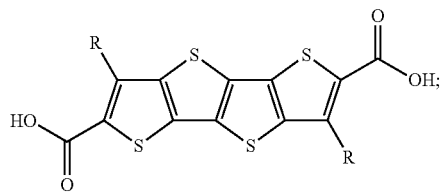
(IV)

and decarboxylating the diacid (IV) to provide the β"-di-R-substituted fused thiophene of the formula (V):

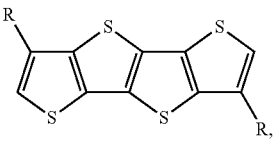
(V)

where R is independently a substituted or unsubstituted, branched or unbranched, $C_4$ to $C_{25}$ hydrocarbylene.

The R can be, for example, a substituted or unsubstituted hydrocarbylene having from 4 to 25 carbon atoms, having from 8 to 22 carbon atoms, having from 10 to 21 carbon atoms, and like R substituents, including intermediate values and ranges. The examples below demonstrate the present preparative method for making a symmetrical β"-di-R-substituted fused thiophene compound where R can be, for example, —$C_{10}H_{21}$, —$C_{17}H_{35}$, or —$C_{21}H_{43}$. The di-acylation can be accomplished, for example, with at least two equivalents of an alkyl acyl halide, or like synthon, including a slight excess of the reactant.

In embodiments, the alkyl acyl halide can be, for example, $C_{1-17}H_{35}$—(C=O)—Cl. The contacting for the in situ bis-ring formation can be accomplished, for example, with at least two equivalents of 2-mercapto ethyl acetate. The decarboxylation of the diacid (IV) can be accomplished, for example, with a heated mixture of cuprous oxide in a suitable glycol ether solvent, or like solvent. In a specific example, the decarboxylation of the diacid (IV) was accomplished by heating a mixture of $Cu_2O$ in tetraethyleneglycol dimethylether at about 220 to 240° C.

In a specific example, the β"-di-R-substituted fused thiophene (V) compound prepared was 3,7-diheptadecyl thieno[3,2-b]thieno[2',3':4,5]thieno[2,3-d]thiophene (DC17FT4). In another specific example, the β"-di-R-substituted fused thiophene (V) compound prepared was 3,7-didecyl thieno[3,2-b]thieno[2',3':4,5]thieno[2,3-d]thiophene (DC10FT4). In another specific example, the β"-di-R-substituted fused thiophene (V) compound prepared was 3,7-diheneicosyl thieno[3,2-b]thieno[2',3':4,5]thieno[2,3-d]thiophene (DC21FT4). The β"-di-R-substituted fused thiophene compounds disclosed and prepared include all intermediates and equivalents thereof, including combinations thereof, and salts thereof.

The disclosure provides an improved route to preparing DCXFT4 and like compounds based on experimentally demonstrated preparation of DC17FT4, DC10FT4, and DC21FT4.

The disclosed process eliminates unnecessary steps including, for example, elimination of an alcohol-to-aldehyde oxidation. Instead, commercially available acid chlorides are selected for introducing the carbonyl functionality —(C=O)—. The disclosed process also eliminates, for example, a diol to diketone oxidation. Instead, the reaction of tetrabromothienothiophene and an acid chloride directly gives a diketone product. The disclosed process also includes an improved decarboxylation to provide a DCXFT4 core in the final step (see Shchekotikhin, A. E., et al., *Chem Heterocycl Comp.* 2007, 43, 439).

In embodiments, the disclosed process provides a DC17FT4 product by, for example, the steps of: diketone formation (e.g., 44% yield), cyclization to construct the four fused rings (e.g., 84% yield), hydrolysis of the diester to the diacid (96% yield), and decarboxylation (e.g., 85% yield), in an overall yield of about 30%. Further yield improvements are being developed, especially for the diketone formation step.

Particularly useful aspects of the disclosed method compared to a prior art method can be, for example, shorter synthetic route (four steps compared to at least six or more), a higher overall yield of about 30% versus about 18%. Each intermediate (diketone, diester, and diacid) has been obtained in a higher crude yield when compared with the prior method. This in turn provides simpler purification and decreased process time and cost. The disclosed preparative method also avoids the use of a chromium oxidizing reagent and a quinoline solvent used in the prior method.

DC17FT4 is a key precursor for preparing semi-conducting polymers of the form PQDC17FT4. (where Q=any co-monomer) (see He, M.; et al., *J. Am. Chem. Soc.* 2009, 131, 11930; Fong, H., et al., *J. Am. Chem. Soc.* 2008, 130, 13202; He, M., et al., *J. Org. Chem.*, 2007, 72, 442; Patent App. WO2008106019). A synthesis of DC17FT4 from the straight chain $C_{18}$ alcohol and tetrabromothienothiophene has been previously disclosed ("prior process"), see commonly owned and assigned, U.S. Pat. No. 7,705,108 (ibid.), and as illustrated in Scheme 1.

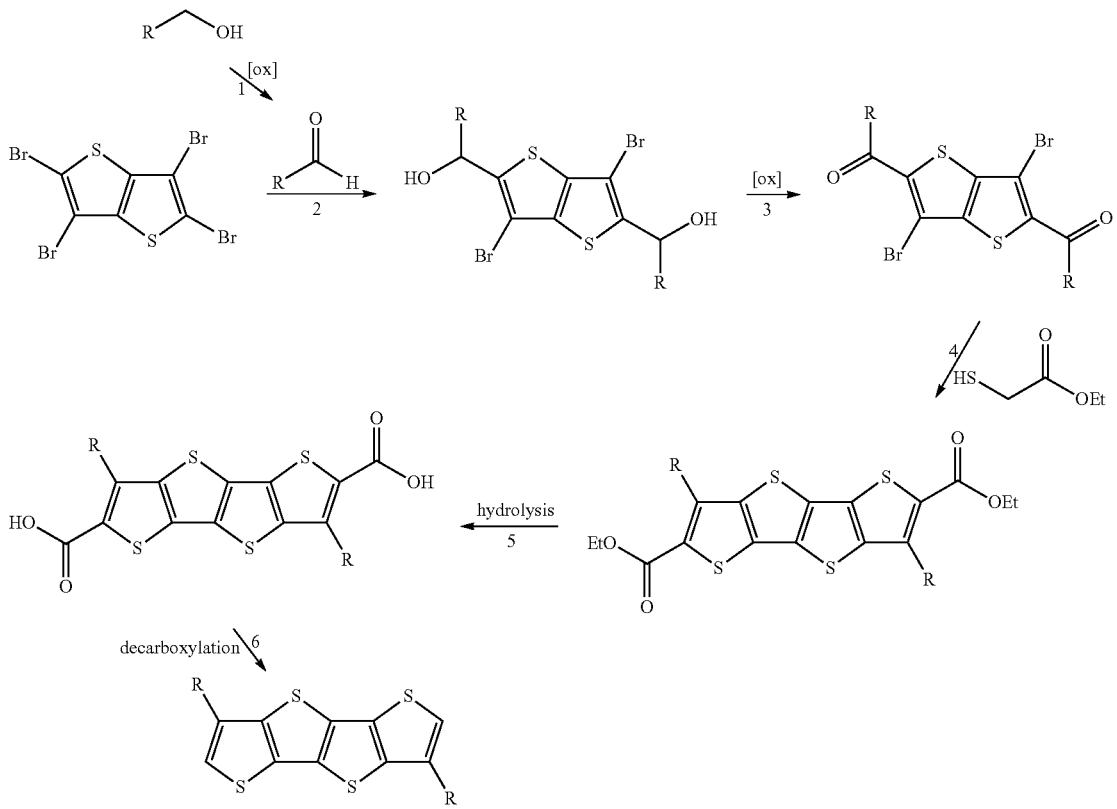

Scheme 1. Prior DCXFT4 preparative process.

This process used a six step sequence and is believed applicable to form any DCXFT4 (X=17 is the most popular sidechain). Oxidation of the alcohol to aldehyde used PCC (80%) (see Gaikwad, D. D., et al., *India. Org. Chem.*, 2008, 4, 125). Lithium halogen exchange of the tetrabromothienothiophene followed by alkylation with the $C_{18}$ aldehyde gave a diol (84%)(see Patent App. WO2005012326). Oxidation of diol using Jones reagent gave the diketone (62%)(see Harding, K. E., et al., *J. Org. Chem.*, 1975, 40, 1664). A cyclization procedure was used to construct two outer fused rings (72%)(see Frey, J., *Chem. Comm.* 2002, 2424; Frey, J, et al., *Org. Synth.* 2006, 83, 209). Hydrolysis to a diacid (97%) followed by decarboxylation (61%) completed the process (see Frey ibid.).

The prior process gave DC17FT4 in about a 17.6% overall yield. However, shortcomings of the prior process can include, for example: an environmentally unfriendly chromium reagent was used in two steps of the process (see Gavin, I. M., et al., *Environ Mol. Mutagen.* 2007, 48, 650). Quinoline was used in the decarboxylation reaction, which is difficult to remove and can potentially contaminate the product with decomposition products (see Shindo, H., et al., *Heterocycles*, 1989, 29, 899; Frey, J., et al., *Org. Synth.*, 2006, 83, 209). The decarboxylation step also used high temperatures (270-300° C.). This prior procedure gave lower overall yields of, for example, from about 15 to about 20 percent. The presently disclosed improved procedure provides a process which avoids or mitigates the aforementioned shortcomings.

In embodiments, the disclosure provides an improved process for preparing DCXFT4 as illustrated in Scheme 2.

compound can be named: 3,7-diheptadecyl thieno[3,2-b]thieno[2',3':4,5]thieno[2,3-d]thiophene or 5,12-diheptadecyl-3,7,10,14-tetrathiatetracyclo[6.6.0.0$^{2,6}$.0$^{9,13}$]tetradeca-1(8),2(6),4,9(13),11-pentaene. When the R substituents are

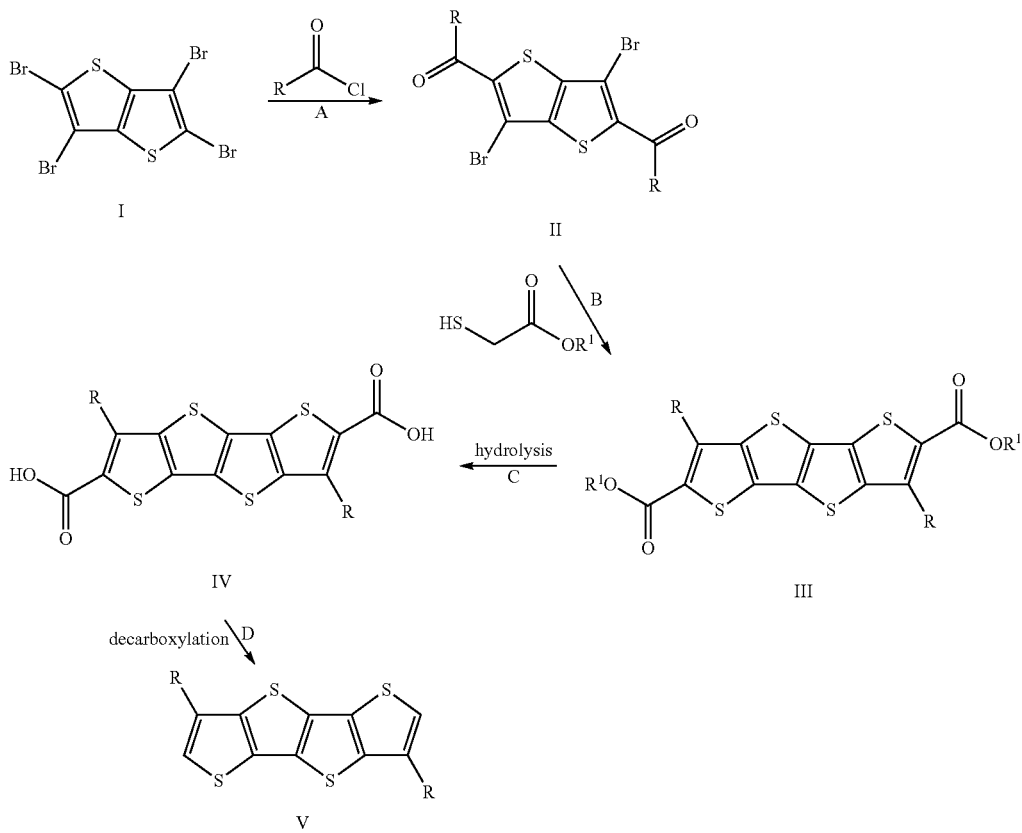

Scheme 2. Improved preparative process to DCXFT4 compounds.

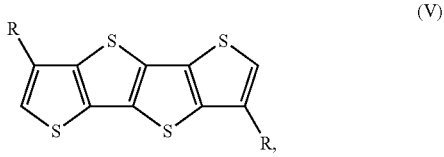

The disclosed process replaces steps 1, 2 and 3 of the prior process of Scheme 1 with step A (Scheme 2). Steps 4 and 5 of the prior process of Scheme 1 remain unchanged and are represented in Scheme 2 by steps B and C. The final decarboxylation step D in Scheme 2 has also been improved compared to the prior process Step 6, by using different reagents which afford better results.

Specific DCXFT4 compounds prepared include, for example:

DC10FT4, DC17FT4, and DC21FT4, of the formula (V):

(V)

where the identical and C$_2$ symmetric (i.e., about the FT4 core) R substituents are, respectively: —C$_{10}$H$_{21}$, —C$_{17}$H$_{35}$, and —C$_{21}$H$_{43}$. When the R substituents are —C$_{10}$H$_{21}$, this compound can be named: 3,7-didecyl thieno[3,2-b]thieno[2',3':4,5]thieno[2,3-d]thiophene or 5,12-didecyl-3,7,10,14-tetrathiatetracyclo[6.6.0.0$^{2,6}$.0$^{9,13}$]tetradeca-1(8),2(6),4,9(13),11-pentaene. When the R substituents are C$_{17}$H$_{35}$, this —C$_{21}$H$_{43}$, this compound can be named: 3,7-diheneicosyl thieno[3,2-b]thieno[2',3':4,5]thieno[2,3-d]thiophene or 5,12-diheneicosyl tetrathiatetracyclo[6.6.0.0$^{2,6}$.0$^{9,13}$]tetradeca-1(8),2(6),4,9(13),11-pentaene.

In embodiments, the disclosure provides a device including at least one of the disclosed monomer compounds, or a polymer thereof. The device including, for example, a photovoltaic, an electroluminescent display, a sensor, a transistors, a semiconductor, an RFID tag, a light-emitting diode, or a combination thereof.

In embodiments, the disclosure provides a preparative processes for an FTx compound to FT(x+2) ring system extension and beta-di-substituent elaboration, for example, an FT2 compound to an FT4 ring system extension and beta-di-substituent elaboration. The disclosed preparative process can be readily applied to, for example, analogous systems, such as an FT3 compound to FT5 ring system extension and beta-di-substituent elaboration, an FT4 compound to FT6 ring system extension and beta-di-substituent elaboration, and like extension applications. The analogous ring system extended compounds can also be selected for further substituent derivatization or polymerization.

EXAMPLES

The following examples serve to more fully describe the manner of using the above-described disclosure, and to further set forth the best modes contemplated for carrying out various aspects of the disclosure. It is understood that these examples do not limit the scope of this disclosure, but rather are presented for illustrative purposes. The working examples further describe how to prepare the hybrids of the disclosure.

Example 1

Di-acylation (Step A) A suspension of 2,3,5,6-tetrabromothieno[3,2,b]thiophene (9.1 g, 0.2 mol) in anhydrous THF (500 mL) was cooled to −78° C. Phenyl lithium solution in n-butyl ether (1.8 mol/L, 24 mL, 2.16 eq.) was added dropwise and the reaction mixture was stirred at −78° C. After 1 hr, an aliquot was removed and quenched, then tested by GC-MS. This test revealed that the di-anion was formed in 100% yield. Stearoyl chloride (13.6 g, 0.045 mol) was dissolved in tetrahydrofuran (THF) and added as quickly as possible while maintaining the reaction temperature as close to −78° C. as possible. The reaction was allowed to warm to RT over a few hours and then stirred overnight at RT. The reaction mixture was then quenched with water (2.5 to 3 eq.). The solvent was then removed under reduced pressure and the residual solid was washed with water (2×300 mL) and methanol (2×300 mL), filtered, then dried. The crude product was recrystallized from hot to cold hexane to give the desired product, 1-{3,6-dibromo-5-octadecanoylthieno[3,2-b]thiophen-2-yl}octadecan-1-one (7.3 g, 44% yield) as an off white solid. $^1$H NMR (CD$_2$Cl$_2$) δ 0.88 (6 H, t, J=6.6 Hz), 1.20-1.48 (56 H, m), 1.69-1.82 (4 H, m), and 3.07 (4 H, t, J=7.2 Hz).

Example 2

Bis-Annulation (Step B) The 1-{3,6-dibromo-5-octadecanoylthieno[3,2-b]thiophen-2-yl}octadecan-1-one (30.0 g, 36 mmol) product of Example 1 was mixed with K$_2$CO$_3$ (50 g, 360 mmol) and N,N-dimethylformamide (100 mL). The mixture was heated to 60° C. and ethyl 2-mercaptoacetate (8.8 mL, 79 mmol) was added dropwise. The reaction mixture was stirred for 48 hours at 60° C. under nitrogen, then was poured into ice water (500 mL). The crude product was filtered from the solution and washed with water, MeOH, then acetone twice, to give the product 2,6-dicarboethoxy-3,7-diheptadecylthieno[3,2-b]thieno[2',3':4,5]thieno[2,3-d]thiophene (26 g, 84% yield). $^1$H NMR (CD$_2$Cl$_2$) δ 0.90 (6 H, t, J=6.6 Hz), 1.27-1.38 (56 H, m), 1.42 (6 H, t, J=7.2 Hz), 1.73-1.87 (4 H, m), 3.20 (4 H, t, J=7.5 Hz), and 4.39 (4 H, q, J=7.2 Hz).

Example 3

Ester deprotection (Step C) The 2,6-dicarboethoxy-3,7-diheptadecylthieno[3,2-b]thieno[2',3':4,5]thieno[2,3-d]thiophene (26.0 g, 30 mmol) product of Example 2, LiOH (2.9 g, 121 mmol in 29 mL water), THF (100 mL), MeOH (20 mL) and a catalytic amount (about 35 mg) of tetrabutylammonium bromide were combined in a round bottomed flask fitted with a condenser and heated at reflux overnight. Approximately 90% of the solvent was evaporated and the residue was acidified to pH 1 with concentrated hydrochloric acid to form a solid which was collected by filtration, washed thoroughly with water and methanol, and dried under vacuum to yield 3,7-diheptadecanyl thieno[3,2-b]thieno[2':3':4,5]thieno[2,3-d]thiophene-2,6-dicarboxylic acid (23.5 g, 96% yield). $^1$H NMR (D$_8$-THF) δ 0.88 (6H, m), 1.20-1.50 (72H, m), 1.70-1.87 (4H, m), and 3.23 (4H, m).

Example 4

Decarboxylation (Step D) A mixture of the 3,7-diheptadecanyl thieno[3,2-b]thieno[2',3':4,5]thieno[2,3-d]thiophene-2,6-dicarboxylic acid (29 g, 35.5 mmol) product of Example 3, Cu$_2$O (1.16 g, 0.2 eq.) and glycine (1.16 g, 0.3 eq.) in tetraethyleneglycol dimethylether (600 mL) was heated to about 220 to 230° C. in a flask fitted with an outlet bubbler to monitor gas evolution. As the decarboxylation proceeded the evolved gas was monitored periodically. After 2.5 hr no further gas evolved and the reaction was terminated after 3 hr total. The hot reaction mixture was filtered quickly to remove the copper oxide and other solid residue. The filtered solution was then cooled to RT, to afford a pale yellow precipitate (24 g, 96%). This was filtered from the solution and recrystallized hot to cold from toluene to give the desired product, 3,7-diheptadecyl thieno[3,2-b]thieno[2',3':4,5]thieno[2,3-d]thiophene (DC17FT4) (22 g, 85% yield) as an off white solid. $^1$H NMR (CD$_2$Cl$_2$) δ 0.91 (6H, t, J=6.6 Hz), 1.29-1.46 (56H, m), 1.74-1.88 (4 H, m), 2.78 (4H, t, J=7.5 Hz), and 7.02 (2H, s).

Example 5-8

Preparation of DC10FT4 Examples 1-4 above were repeated with minor modifications to produce DC10FT4 as described below.

Example 5

Di-acylation (Step A) A suspension of (2,3,5,6-tetrabromothieno[3,2,b]thiophene (10 g, 21.9 mmol) in anhydrous THF (200 mL) was cooled to −78° C. Phenyl lithium solution in n-butyl ether (1.8 mol/L, 25 mL, 45 mmol) was added dropwise and the reaction mixture was stirred at −78° C. for 4 h. Undecanoyl chloride (9.2 g, 44.9 mmol) was added to the reaction mixture via syringe while maintaining the temperature of the mixture as close to −78° C. as possible. The reaction was allowed to warm to RT over about three hours and then stirred overnight at RT. The reaction mixture was then quenched by the addition of crushed ice (200 g). The reaction mixture was stirred while the ice was allowed to melt. Most (greater than about 90%) of the THF was then removed under reduced pressure and the solid was filtered from the residual solution. The solid was suspended in water (100 mL) and stirred for 1 hr then filtered. The solid was resuspended in methanol (100 mL), stirred for 1 hr then filtered to give the product 1-{3,6-dibromo-5-undecanoylthieno[3,2-b]thiophen-2-yl}undecan-1-one as a white solid (5.75 g, 41.3% yield). $^1$H NMR (CD$_2$Cl$_2$) δ 0.90 (6H, t, J=6.3 Hz), 1.20-1.48 (28H, m), 1.68-1.73 (4H, m), and 3.11 (4H, t, J=7.2 Hz).

Example 6

Bis-Annulation (Step B) The 1-{3,6-dibromo-5-octadecanoylthieno[3,2-b]thiophen-2-yl}octadecan-1-one (6 g, 9.46 mmol) product of Example 5 was dissolved in N,N-dimethylformamide (150 mL) and stirring was started. Potassium carbonate (13.06 g, 94.6 mmol) was added at a rate such that the stirring was not disrupted followed by the addition of 18-crown-6 (10 mg). The mixture was heated to 80° C. and ethylthioglycolate (2.27 g, 18.91 mmol) was added dropwise. The reaction mixture was stirred for 72 hours at 80° C. under nitrogen. Crushed ice (170 g) was added and the reaction mixture was allowed to stir for 1 hr. The solid was filtered from the solution the re-suspended in water (200 mL) and stirred for 1 hr. The suspension was filtered again and the solid re-suspended in methanol (200 mL) and stirred for another 1 hr. The solid was filtered from the methanol solution and dried under vacuum to give the product 2,6-dicarboethoxy-3,7- diheptadecylthieno[3,2-b]thieno[2',3':4,5]thieno[2,3-d]thiophene (5.00 g, 78.2% yield). $^1$H NMR (CD$_2$Cl$_2$) δ 0.87 (6H, t, J=6.3 Hz), 1.15-1.35 (28H, m), 1.40 (6H, t, J=7.2 Hz), 1.68-1.82 (4H, m), 3.17 (4H, t, J=7.2 Hz), and 4.36 (4H, q, J=7.2 Hz).

Example 7

Ester deprotection (Step C) The 2,6,-dicarboethoxy-3,7-diheptadecylthieno[3,2-b]thieno[2',3':4,5]thieno[2,3-d]thiophene (5.00 g, 7.39 mmol) product of Example 6, was dissolved in tetrahydrofuran (THF) (280 mL) then methanol (40 mL) was added. Lithium hydroxide (707 mg, 29.5 mmol) was dissolved in water (7 mL) and added to the stirred methanol and THF solution. A condenser was fitted and the reaction mixture was heated in an oil bath at 90° C. for 16 hr. The THF and methanol were removed under reduced pressure. 60 mL of methanol and 10 mL of conc. hydrochloric acid were added then stirred for 4 h. Next 50 mL of water was added and the solid was filtered off. The product was dried under vacuum to give the 3,7-didecanyl thieno[3,2-b]thieno[2',3':4,5]thieno[2,3-d]thiophene-2,6-dicarboxylic acid (4.50 g, 98% yield). $^1$H NMR (D$_8$-THF)(of the di-lithium salt) δ 0.88 (6H, t, J=6.9 Hz), 1.20-1.47 (28H, m), 1.70-1.86 (4H, m), and 3.24 (4H, t, J=7.5 Hz).

Example 8

Decarboxylation (Step D) A mixture of the 3,7-didecanyl thieno[3,2-b]thieno[2',3':4,5]thieno[2,3-d]thiophene-2,6-dicarboxylic acid (0.50 g, 0.8 mmol) product of Example 7, Cu$_2$O (10 mg, 0.07 mmol), and glycine (10 mg, 0.13 mmol) in tetraethyleneglycol dimethylether (40 mL) was heated to about 240° C. in a flask fitted with an outlet bubbler to monitor gas evolution. As the decarboxylation proceeded the evolved gas was periodically monitored. After 1.5 hr no further gas evolved and after 2 hr total the reaction was terminated. The hot reaction mixture was filtered quickly to remove the copper oxide and other solid residue. The filtered solution was then cooled to RT, to afford a pale yellow precipitate (4.1 g, 96%). This was filtered from the solution and subsequently recrystallized hot to cold from toluene to give the desired product, 3,7-didecylthieno[3,2-b]thieno[2',3':4,5]thieno[2,3-d]thiophene (DC10FT4) (3.9 g, 91% yield) as an off white solid. $^1$H NMR (CD$_2$Cl$_2$) δ0.88 (6H, t, J=6.9 Hz), 1.20-1.45 (28H, m), 1.68-1.80 (4H, m), 2.75 (4H, t, J=7.5 Hz), and 7.00 (2H, s).

Example 9-12

Preparation of DC21FT4 Examples 1-4 above can be repeated with minor modifications to produce DC21FT4 described below.

Example 9

Di-acylation (Step A) A suspension of (2,3,5,6-tetrabromothieno[3,2,b]thiophene (20 mmol) in anhydrous THF (200 mL) is cooled to −78° C. Phenyl lithium solution in n-butyl ether (41 mmol) is added dropwise and the reaction mixture is stirred at −78° C. for 4 h. Docosanoyl chloride (41 mmol) is added to the reaction mixture via syringe while maintaining the temperature of the mixture as close to −78° C. The reaction is allowed to warm to RT over about three hours and then stirred overnight at RT. The reaction mixture is then quenched by the addition of crushed ice (200 g). The reaction mixture is stirred while the ice is allowed to melt. Most (>90%) of the THF is then removed under reduced pressure and the solid is filtered from the residual solution. The solid is suspended in water (100 mL) and stirred for 1 hr then filtered. The solid is re-suspended in methanol (100 mL), stirred for 1 hr then filtered to give the product 1-{3,6-dibromo-5-docosanoylthieno[3,2-b]thiophen-2-yl}docosan-1-one. $^1$H NMR (CD$_2$Cl$_2$) δ 0.95-1.15 (6H, m), 1.30-1.82 (76H, m) and 3.17-3.32 (4H, m).

Example 10

Bis-Annulation (Step B) The 1-{3,6-dibromo-5-docosanoylthieno[3,2-b]thiophen-2-yl}docosan-1-one (10 mmol) product of Example 9 is dissolved in N,N-dimethylformamide (150 mL) and stirring is started. Potassium carbonate (100 mmol) is added at a rate such that the stirring is not disrupted followed by the addition of 18-crown-6 (10 mg). The mixture is heated to 80° C. and ethylthioglycolate (20 mmol) is added dropwise. The reaction mixture is stirred for 72 hours at 80° C. under nitrogen. Crushed ice (170 g) is added and the reaction mixture is allowed to stir for 1 hr. The solid is filtered from the solution then re-suspended in water (200 mL) and stirred for 1 hr. The suspension is filtered again and the solid re-suspended in methanol (200 mL) and stirred for another 1 hr. The solid is filtered from the methanol solution and dried under vacuum to give the product 2,6-dicarboethoxy-3,7-diheneicosylthieno[3,2-b]thieno[2',3':4,5]thieno[2,3-d]thiophene. $^1$H NMR (D$_8$-THF) δ 0.89 (6H, t, J=6.3 Hz), 1.02-1.60 (78H, m) 1.60-1.84 (4H, m), 3.10-3.30 (4H, m), and 4.24-4.42 (4H, m).

Example 11

Ester deprotection (Step C) The 2,6,-dicarboethoxy-3,7-diheneicosylthieno[3,2-b]thieno[2',3':4,5]thieno[2,3-d]thiophene (10 mmol) product of Example 10, is dissolved in tetrahydrofuran (THF) (280 mL) then methanol (40 mL) is added. Lithium hydroxide (40 mmol) is dissolved in water (10 mL) and added to the stirred methanol and THF solution. A condenser is fitted and the reaction mixture is heated in an oil bath at 90° C. for 16 hr. The THF and methanol are removed under reduced pressure. 60 ml, of methanol and 10 mL of conc. hydrochloric acid are added then stirred for 4 h. Next 50 mL of water is added and the solid is filtered off. The product is dried under vacuum to give the 3,7-diheneicosyl thieno[3,2-b]thieno[2',3':4,5]thieno[2,3-d]thiophene-2,6-dicarboxylic acid. $^1$H NMR (D$_8$-THF) δ 0.89 (6H, t, J=6.9 Hz), 1.17-1.45 (72H, m), 1.68-1.85 (4H, m), and 3.18-3.28 (4H, m).

Example 12

Decarboxylation (Step D) A mixture of the 3,7-diheneicosyl thieno[3,2-b]thieno[2',3':4,5]thieno[2,3-d]thiophene-2,6-dicarboxylic acid (1.0 mmol) product of Example 11, Cu$_2$O (0.10 mmol), and glycine (0.16 mmol) in tetraethyleneglycol dimethylether is heated to about 240° C. in a flask fitted with an outlet bubbler to monitor gas evolution. As the decarboxylation proceeds the evolved gas is periodically monitored. After about 1.5 hr no further gas is observed to evolve and after 2 hr total the reaction is terminated. The hot reaction mixture is filtered quickly to remove the copper oxide and other solid residue. The filtered solution is then cooled to RT, to afford a pale yellow precipitate. This is filtered from the solution and subsequently recrystallized hot to cold from toluene to give the desired product, 3,7-diheneicosylthieno[3,2-b]thieno[2',3':4,5]thieno[2,3-d]thiophene (DC21FT4)

$^1$H NMR (CD$_2$Cl$_2$) δ0.91 (6H, t, J=6.8 Hz), 1.15-1.50 (76H, m), 1.74-1.90 (4H, m), 2.78 (4H, m), and 7.02 (2H, s).

Example 13

Polymer preparation—Poly(3,7-didecylthieno[3,2-b]thieno[2',3':4,5]thieno[2,3-d]thiophene) A fused thiophene polymer of 3,7-didecylthieno[3,2-b]thieno[2',3':4,5]thieno[2,3-d]thiophene is made using the general procedure described below. This procedure is adapted from Anderson, et al., *Macromolecules* 1994, 27, 6506, which is incorporated herein by reference.

3,7-didecylthieno[3,2-b]thieno[2',3':4,5]thieno[2,3-d]thiophene (10 mmol) product of Example 8 is dissolved in 30 mL chlorobenzene. A suspension of ferric chloride (2.5 mmol) in 20 mL chlorobenzene is added to the monomer solution over 30 min. The mixture is allowed to stir for several (e.g., from about 6 to about 24) hours at room temperature. It may be desirable to heat the reaction mixture at about 80 to about 90° C. for several hours for fused thiophene monomer compounds having larger (e.g., 4 or greater) numbers of rings in their fused ring system. The reaction mixture is then precipitated from a 500 mL mixture of 95:5 methanol:water. The precipitate is collected by filtration, dissolved in toluene, boiled with concentrated ammonia (3×60 mL), and boiled with ethylene diamine tetraacetic acid (0.05 M in water, 2×50 mL). The organic layer is precipitated from methanol (500 mL). Filtration and vacuum drying (70-80° C.) yields polymeric material.

Example 14

Bromination of 2,6-dibromo-3,7-didecanyltetrathienoacene. The 3,7-didecanyltetrathienoacene (1 mmol) product of Example 8 is dissolved in methylene chloride (60 mL). N-bromosuccinimide (NBS) (2.02 mmol) is dissolved in DMF (20 mL) and is added dropwise to the flask in the dark. The resulting mixture is stirred overnight in the dark. The methylene chloride is evaporated and the remaining solid residue is washed with water (3×100 mL) and methanol (50 mL). The solid is dried and re-crystallized from hexane to give 2,6-dibromo-3,7-didecanyltetrathienoacene. $^1$H NMR (CD$_2$Cl$_2$) δ0.88 (6H, t, J=6.9 Hz), 1.18-1.43 (28H, m), 1.64-1.82 (4H, m) and 2.78 (4H, t, J=7.5 Hz).

Example 15

Polymer Preparation—Poly(2,5-bis(thiophene-2-yl)-(3,7-didecanyltetrathienoacene) (P2TDC10FT4).). The 2,6-dibromo-3,7-didecanyltetrathienoacene (1 mmol) product of Example 14 and 1,1'-[2,2'-bithiophene]-5,5'-diylbis[1,1,1-trimethylstannane] (1 mmol) are dissolved into toluene (30 mL) in a flask. Nitrogen is bubbled through the contents of the flask for several minutes. Tetrakis(triphenylphosphine)palladium(0) (0.09 g, 0.785 mmol) is added to this mixture. The mixture is heated to 125-130° C. under nitrogen for 16 hrs. The mixture is poured into a methanol (400 mL) and concentrated hydrochloric acid (20 mL) solution and stirred overnight at room temperature. The precipitate is filtered and Soxhlet extracted with acetone and hexane for 24 hr each. The obtained polymer is then dissolved into chlorobenzene, filtered, and precipitated in methanol. The collected polymer is dried in vacuum.

The disclosure has been described with reference to various specific embodiments and techniques. However, it should be understood that many variations and modifications are possible while remaining within the spirit and scope of the disclosure.

What is claimed is:

1. A method for making a β"-di-R-substituted fused thiophene compound, comprising:
    di-acylating tetra-bromo dithiophene of the formula (I):

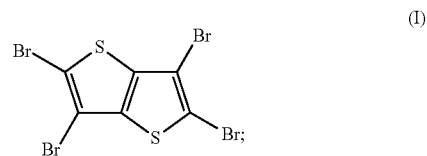

contacting the resulting α-di-acyl-β-di-bromo-dithiophene compound of the formula (II):

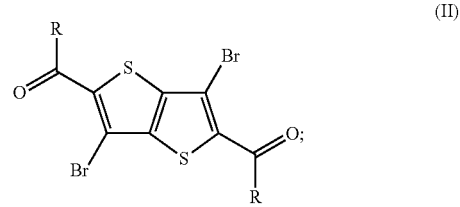

with a 2-mercaptoacetate to form the cyclized α"-carboxy-β"-di-R-substituted fused thiophene of the formula (III):

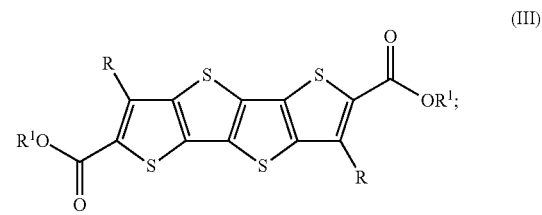

converting the α"-carboxy-β"-di-R-substituted fused thiophene (III) to the corresponding diacid of the formula (IV):

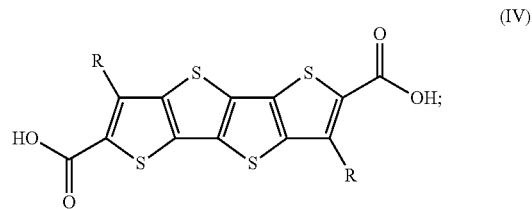

and
decarboxylating the diacid (IV) to provide the β"-di-R-substituted fused thiophene of the formula (V):

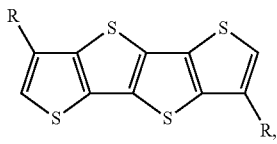

where each R is independently a substituted or unsubstituted, branched or unbranched $C_4$ to $C_{25}$ hydrocarbylene, and $R^1$ is independently a substituted or unsubstituted, branched or unbranched $C_1$ to $C_6$ hydrocarbylene.

2. The method of claim 1 wherein each R is the same substituted or unsubstituted hydrocarbylene having from 4 to 25 carbon atoms.

3. The method of claim 1 wherein each R is the same —$C_{10}H_{21}$, —$C_{17}H_{35}$, or —$C_{21}H_{43}$.

4. The method of claim 1 wherein di-acylating is accomplished with at least two equivalents of an alkyl acyl halide.

5. The method of claim 4 wherein the alkyl acyl halide is $C_{17}H_{35}$—(C=O)—Cl.

6. The method of claim 1 wherein contacting is accomplished with at least two equivalents of 2-mercapto ethyl acetate.

7. The method of claim 1 wherein decarboxylating the diacid (IV) is accomplished by heating a mixture of an copper oxide of Cu(0), Cu(I), or a combination thereof, in a glycol ether solvent.

8. The method of claim 7 wherein the copper oxide is $Cu_2O$, the glycol ether is tetraethyleneglycol dimethylether, and the heating is at from about 220 to about 240° C.

9. The method of claim 7 further comprising an amphoteric compound.

10. The method of claim 9 wherein the amphoteric compound is an amino acid.

11. The method of claim 10 wherein the amino acid is glycine.

12. The method of claim 1 wherein the β"-di-R-substituted fused thiophene (V) is
3,7-diheptadecyl thieno[3,2-b]thieno[2',3':4,5]thieno[2,3-d]thiophene,
3,7-didecyl thieno[3,2-b]thieno[2',3':4,5]thieno[2,3-d]thiophene, or
3,7-diheneicosylthieno[3,2-b]thieno[2',3':4,5]thieno[2,3-d]thiophene.

* * * * *